(12) United States Patent
Takai et al.

(10) Patent No.: US 6,818,802 B2
(45) Date of Patent: Nov. 16, 2004

(54) TOPSHEET MADE OF NONWOVEN FABRIC USED IN DISPOSABLE WEARING ARTICLE

(75) Inventors: Hisashi Takai, Kagawa-ken (JP);
Masaki Yoshida, Kagawa-ken (JP);
Hideyuki Ishikawa, Kagawa-ken (JP);
Miou Suzuki, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 181 days.

(21) Appl. No.: 10/013,984

(22) Filed: Oct. 30, 2001

(65) Prior Publication Data
US 2002/0052582 A1 May 2, 2002

(30) Foreign Application Priority Data
Oct. 31, 2000 (JP) .......................................... 2000-333443

(51) Int. Cl.[7] ................................................. A61F 13/15
(52) U.S. Cl. ....................................... 604/383; 604/372
(58) Field of Search ................................ 604/370, 372, 604/383, 385.01; 442/15, 38, 41, 442, 383

(56) References Cited
U.S. PATENT DOCUMENTS
4,741,941 A    5/1988 Englebert et al.
5,470,326 A  * 11/1995 Dabi et al. .................... 604/383
5,824,352 A    10/1998 Yang et al.
5,897,543 A     4/1999 Francis
6,015,936 A  *  1/2000 Takai et al. ................... 604/383
6,048,600 A     4/2000 Hansson
6,117,524 A  *  9/2000 Hisanaka et al. ............ 428/137
6,506,473 B1 *  1/2003 Hisanaka et al. ............ 428/138

FOREIGN PATENT DOCUMENTS
EP    0 995 414 A1   4/2000
EP    1 025 826 A2   8/2000
EP    1 121 916 A2   8/2001
JP    61-176346      8/1986
JP    63-243360     10/1988
WO    WO 94/20054    9/1994

OTHER PUBLICATIONS
European search report mailed Mar. 21, 2002.

* cited by examiner

Primary Examiner—John J. Calvert
Assistant Examiner—C. Lynne Anderson
(74) Attorney, Agent, or Firm—Butzel Long

(57) ABSTRACT

A topsheet for a disposable wearing article that is formed with a plurality of fine openings each having an area of about 0.16–5 mm$^2$ and a part of the peripheral edge of each opening is protuberated upward from an upper surface of the topsheet. The topsheet is thereby improved so that body fluids can be rapidly absorbed and stuffiness as well as eruption of the wearer's skin can be reliably avoided.

13 Claims, 6 Drawing Sheets

TOPSHEET MADE OF NONWOVEN FABRIC USED IN DISPOSABLE WEARING ARTICLE

BACKGROUND OF THE INVENTION

This invention relates to a topsheet made of nonwoven fabric having a plurality of fine openings suitable for use as a breathable topsheet material or a breathable and liquid-pervious topsheet material in a disposable wearing article such as a disposable diaper, a disposable sanitary napkin, a disposable incontinent pants or a disposable gown used in medical facilities.

Japanese Patent Application Publication No. 1986-176346A describes a topsheet made of a nonwoven fabric adapted to be used in an absorbent article. This topsheet is formed by thermally fusible hydrophobic fibers having a fiber diameter smaller than $10\mu$ and a basis weight of 10 $g/m^2$. The topsheet has an opening ratio of 10–50% and the minimum opening diameter of 0.3–2 mm wherein the fibers are in a melted state around the openings.

Japanese Patent Application Publication No. 1988-243360A describes a nonwoven fabric having a plurality of fine openings arranged in a given pattern. This nonwoven fabric has a nonwoven fabric region with of circular or elliptic openings a wherein the nonwoven fabric region has a substantially uniform density of fiber and a substantially smooth surface. The nonwoven fabric with the above-described openings is made by applying high pressure water-jets in columnar streams to a fibrous web supported on a cylinder having a plurality of projections in semispherical shape.

The nonwoven fabric disclosed in each of the above-identified Publication is intended to be used as a liquid-pervious topsheet in disposable wearing article such as a disposable diaper or a sanitary napkin. The openings formed in the nonwoven fabric are a means to enhance transfer and absorption of body fluids into a liquid-absorbent core covered with this nonwoven fabric. However, when a the wearing article using such nonwoven fabric is worn, the nonwoven fabric having a smooth surface and the wearer's skin may come in close contact with each other so that most of the openings may be closely covered with the wearer's skin and thereby rapid absorption of body fluids may be obstructed. In addition, such close contact of the nonwoven fabric with the wearer's skin may often cause stuffiness and eruption of the wearer's skin.

SUMMARY OF THE INVENTION

The present invention provides a nonwoven fabric that overcomes problems that possibly occur in prior art nonwoven fabrics when used as a topsheet of a disposable wearing article.

It is an object of the present invention to provided a topsheet made of a nonwoven fabric for a disposable wearing article having upper and lower surfaces and formed with a plurality of openings extending through the upper and lower surfaces.

The topsheet has a substantially uniform thickness and each of the openings has an area of about 0.16–5 $mm^2$ wherein only a part of the periphery of the opening is increased in thickness compared to the uniform thickness of the topsheet so as to make the openings protuberate upward from the upper surface.

DETAILED DESCRIPTION OF THE PREFERRED EMBODIMENTS

Details of a topsheet made of a nonwoven fabric according to this invention will be more fully understood from the description of a sanitary napkin as a one embodiment of this invention given hereunder with reference to the accompanying drawings.

Figure 1:
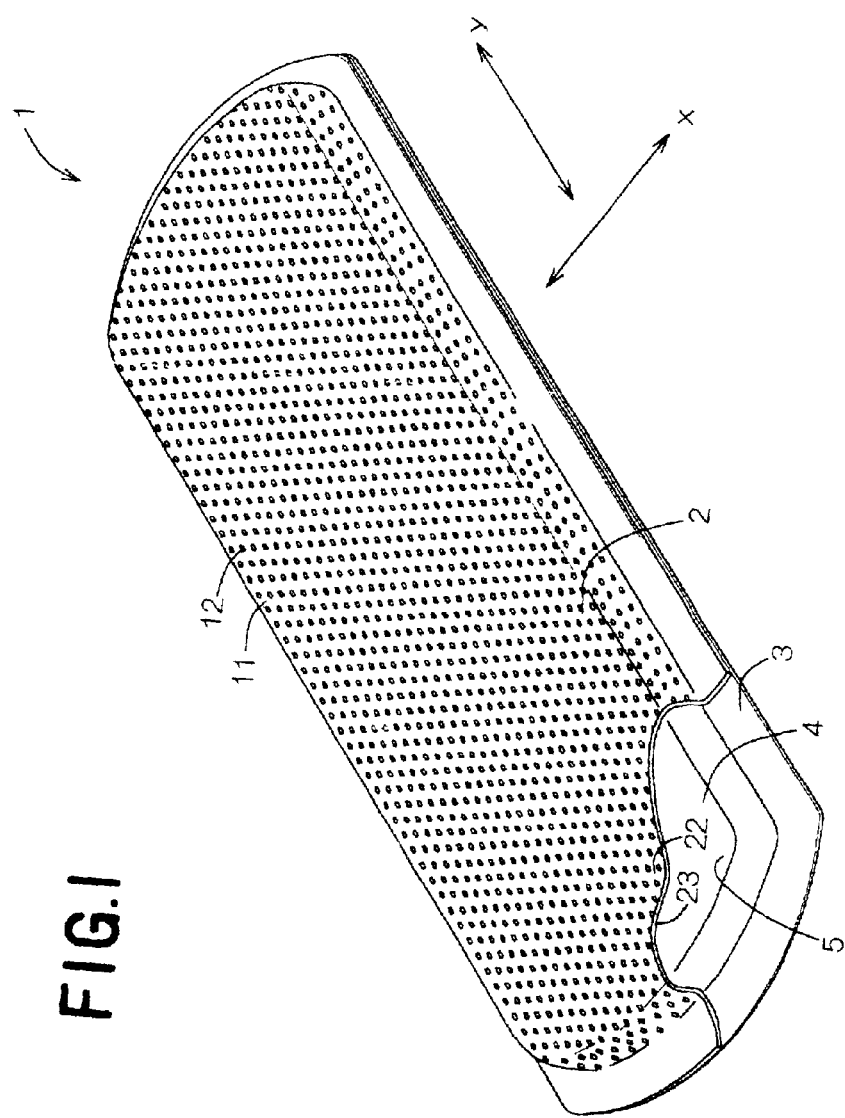
FIG. 1 is a perspective view showing a partially cutaway sanitary napkin.

FIG. 1 is a perspective view showing a partially cutaway sanitary napkin 1 using a topsheet 2 according to this invention. The napkin 1 comprises the liquid-pervious topsheet 2, a liquid-impervious backsheet 3 and a liquid-absorbent core 4 disposed between these two sheets 2, 3 wherein the top- and backsheets 2, 3 extend outward beyond a peripheral edge of the core 4, overlaid to each other and bonded together water-tight in these respective extensions. The napkin 1 is defined by a longitudinal direction y and a transverse direction x, both orthogonal to the direction of its thickness and configured to be larger in the longitudinal direction y.

Figure 2:
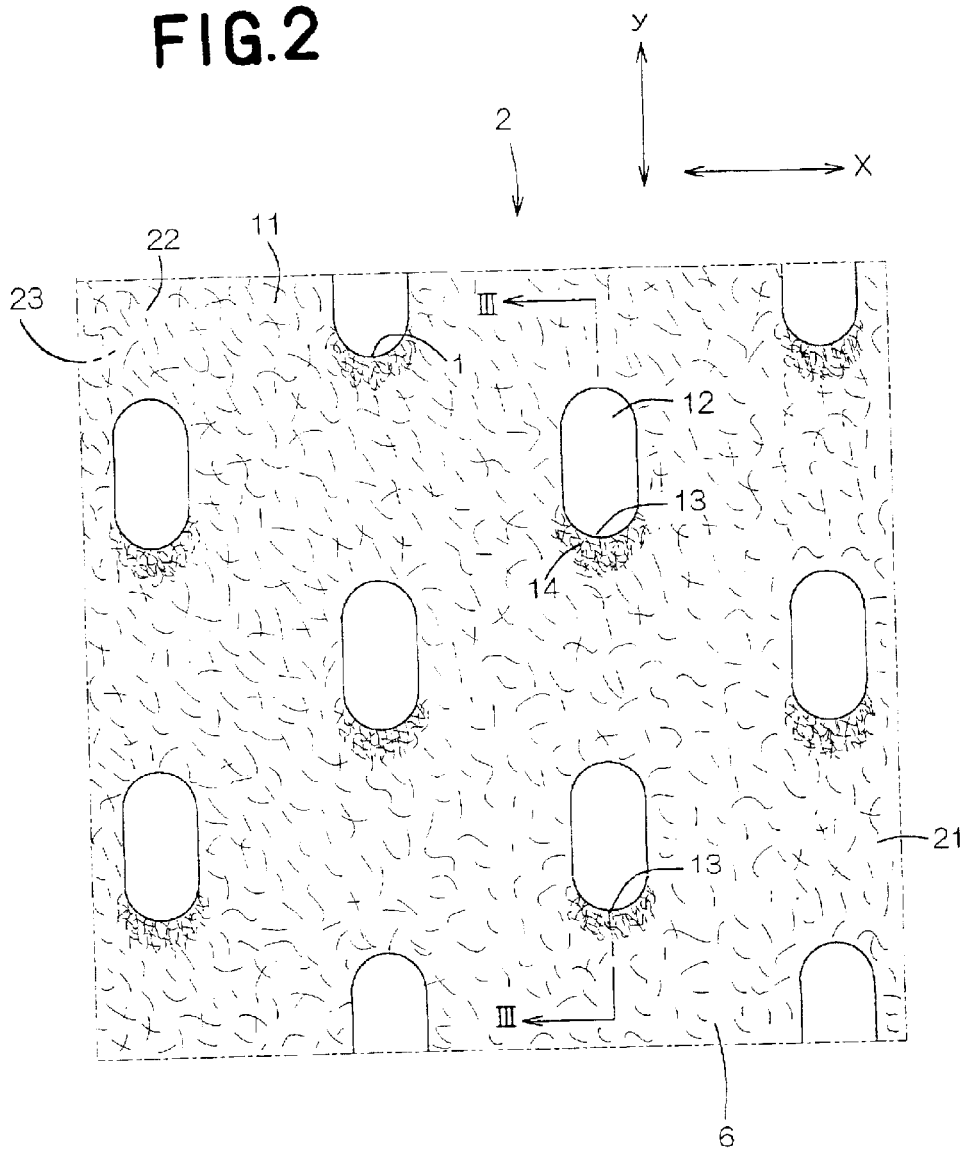
FIG. 2 is a fragmentary enlarged view of a topsheet.

FIG. 2 is a fragmentary enlarged view of a the topsheet 2. The topsheet 2 made of a nonwoven fabric has an upper surface 22 intended to come in contact with the skin of the wearer, a lower surface 23 underlying the core 4, a fibrous zone 11 formed by a plurality of fibers 6 and a plurality of opening zones 12 surrounded by the fibrous zone 11 and extending between the upper and lower surfaces 22, 23 (See FIG. 1 also). The fibrous zone 11 has a basis weight of about 10–100 $g/m^2$ and preferably comprises hydrophobic fibers by about 80–100% by weight and hydrophilic fibers by about 20–0% by weight wherein the hydrophobic fiber is a thermoplastic synthetic fiber having a fineness of about 0.1–10 dtex. Each of the opening zones 12 has an opening area of about 0.16–5 $mm^2$ and the total area of these opening zones 12 entirely occupies about 2–60% of a surface area of the topsheet 2. While the plane shapes as well as the layout of the opening zones 12 on the topsheet 2 are not specified, these opening zones 12 are illustrated to be shaped in elliptic which are larger in the longitudinal direction y and arranged substantially at regular intervals in the longitudinal direction as well as in the transverse direction x.

Figure 3:
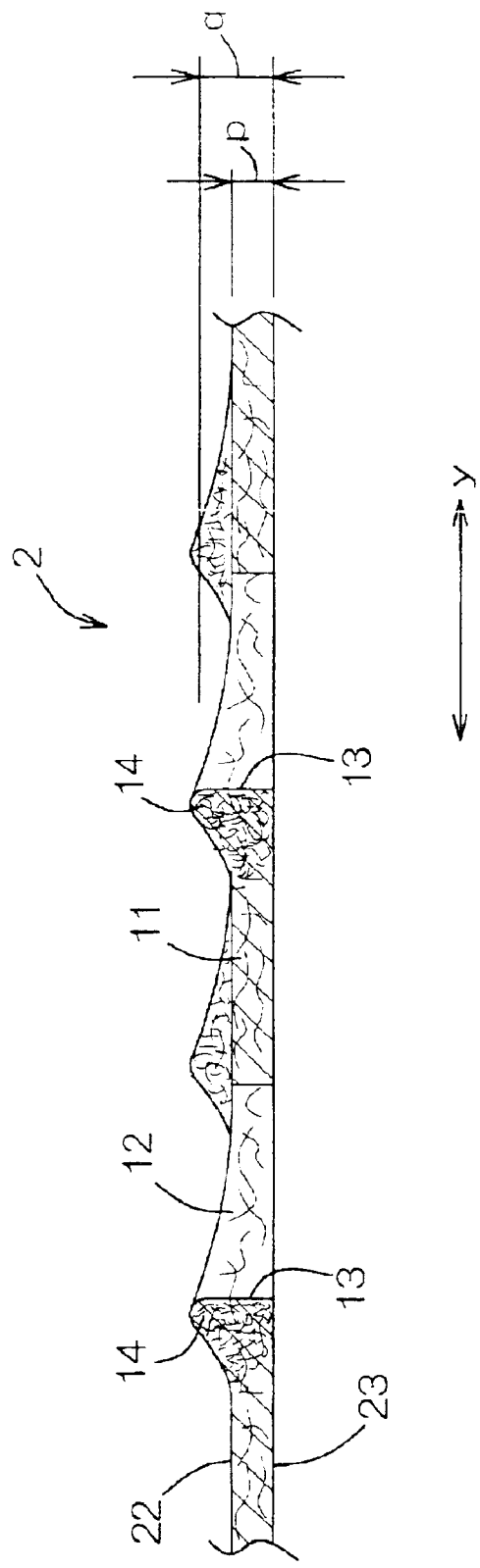
FIG. 3 is a sectional view taken along a line III—III in FIG. 2.

FIG. 3 is a sectional view taken along a line III—III in FIG. 2. While the fibrous zone 11 of the topsheet 2 has a substantially uniform thickness p as a whole, a portion of a peripheral edge defining each of the opening zones 12 extending adjacent its lower end 13 (as viewed in FIG. 2) has a thickness q larger than the thickness p so as to form a protuberance 14 gradually rising above the upper surface of the topsheet 2. The protuberance 14 gradually decreases in thickness along the peripheral edge of the opening zones 12 and along the direction y as viewed in FIG. 2. A range in which the protuberance 14 and its skirt extends along the peripheral edge of the opening zones 12 is preferably equal to about ¼–½ of the entire circumference of the opening zones 12. In such topsheet 2, depending on a particular application thereof, its flat region preferably has a thickness p of about 0.01–5 mm and an apparent density of about 0.01–1.5 g/cm$^3$. Preferably, the protuberance 14 has a thickness q which is larger than the thickness p by about 0.1–2 mm and an apparent density than the density of the flat region by about 1.0–5 times.

When the sanitary napkin 1 using such a topsheet 2 is worn, the topsheet 2 comes in contact with the wearer's skin at crests of each of the protuberances 14 but the opening zones 12 adjacent to the respective protuberance 14 and the plains contiguous to the respective protuberance 14 tend to form a clearance between the topsheet 2 and the wearer's skin and thereby to prevent the opening zones 12 from being closed by the wearer's skin. In this way, menstrual discharge can smoothly flow into the respective opening zones 12 and is rapidly transferred to the core 4. The clearance between the topsheet 2 and the wearer's skin serves to improve ventilation between the topsheet 2 and the wearer's skin. With such sanitary napkin 1, leakage of menstrual discharge as well as stuffiness or eruption can be effectively avoided. The protuberance 14 formed along the peripheral edges of the respective opening zones 12 are particularly effective to prevent the opening zones 12 from being closed by the wearer's skin. The protuberance 14 is formed on the part of the opening zone's peripheral edge which lies aside in the longitudinal direction y toward its lower end 13 as viewed in FIG. 2, so air which would otherwise stay between the topsheet 2 and the wearer's skin can rapidly flow in the longitudinal direction y as well as in the transverse direction x between each pair of the adjacent protuberance 14, 14. It is possible to form the protuberance 14 so as to be put aside in the longitudinal direction y toward the upper end or in the transverse direction x toward one of the side edges of the opening zone's peripheral edge as viewed in FIG. 2. The protuberance 14 is formed to have a density higher than that in the region extending therearound and it is not apprehended that the shape of the protuberance might be easily deformed when the protuberance is pressed against the wearer's skin. The napkin 1 gives somewhat dry touch to its wearer even after absorption of menstrual discharge since the fibrous zone 11 of the topsheet 2 is basically formed by 11 hydrophobic thermoplastic synthetic fiber. It should be understood that the fibrous zone 11 of the topsheet 2 may be treated in desired regions such as the lower surface 23 and/or the peripheral edges of the respective opening zones 12 with an appropriate agent to make these regions hydrophilic.

Figure 4:
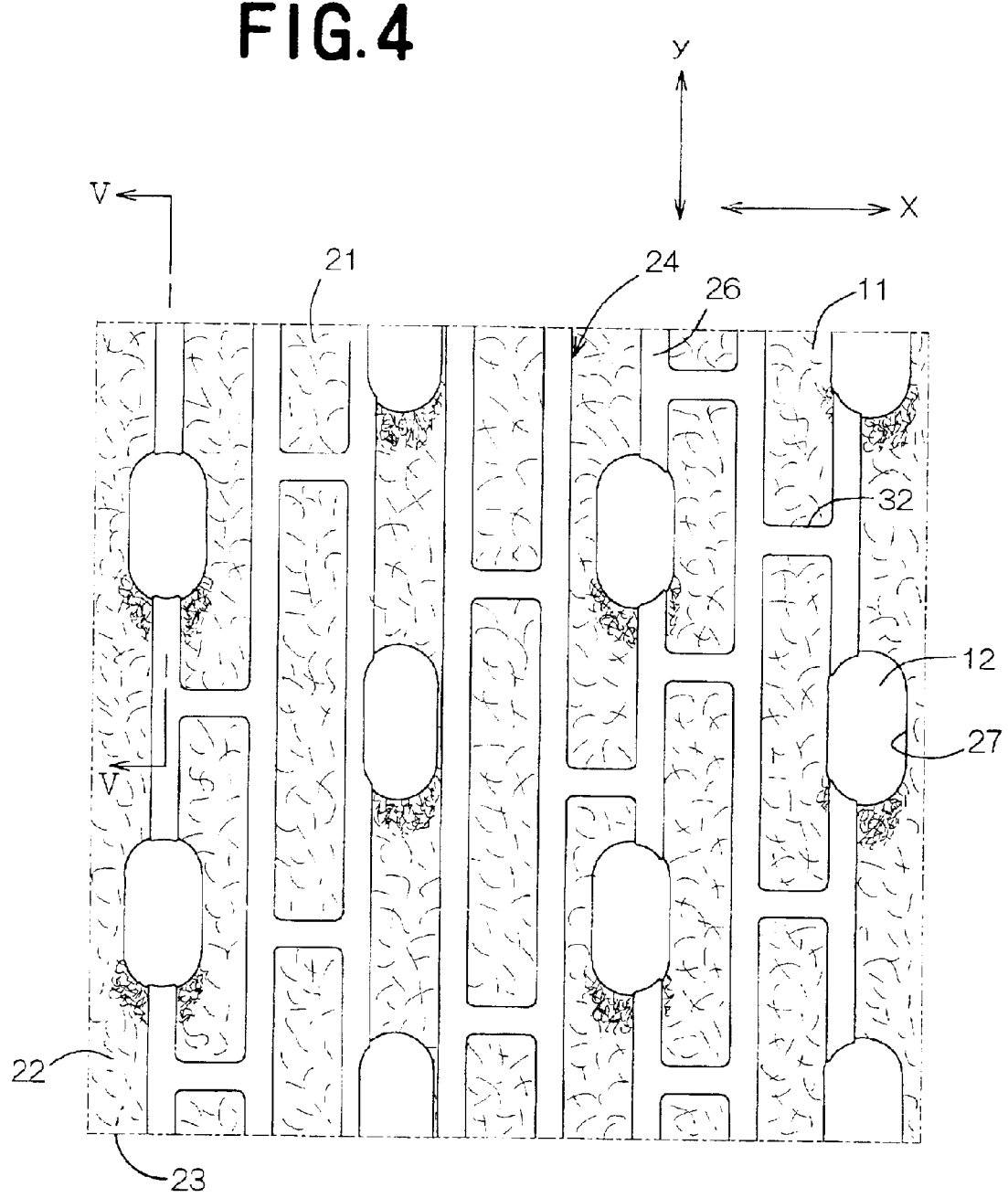
FIG. 4 is a view similar to that in FIG. 2, showing another embodiment of the invention.
Figure 5:
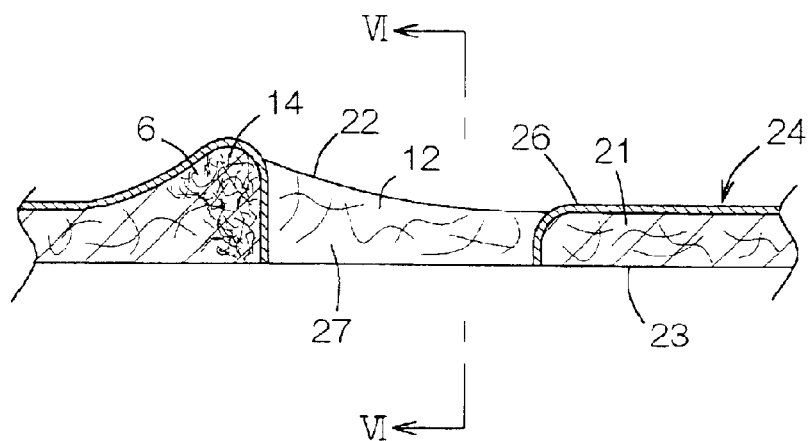
FIG. 5 is a sectional view taken along a line V—V in FIG. 4.
Figure 6:
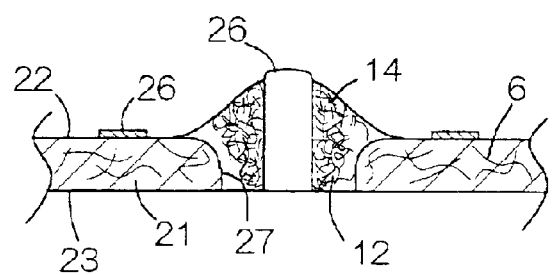
FIG. 6 is a sectional view taken along a line VI—VI in FIG. 5.

FIG. 4 is a view similar to FIG. 2 but showing another embodiment of the invention, FIG. 5 is a sectional view taken along the line V—V in FIG. 4 and FIG. 6 is a sectional view taken along a line VI—VI in FIG. 5. The topsheet 2 according to this embodiment comprises a nonwoven fabric layer 21 having upper and lower surfaces 22, 23 and a thermoplastic synthetic resin film layer 24 bonded to the upper surface 22. The nonwoven fabric layer 21 is similar to the topsheet 2 illustrated by FIG. 2 in that the layer 21 has the fibrous zone 11 and the opening zones 12. The film layer 24 comprises a plurality of ribbon-like strips 26 spaced from and extending in parallel to one another in one direction, for example, in the longitudinal direction y. These ribbon-like strips 26 are welded or bonded by adhesion to the nonwoven fabric layer 21 and interrupted in the longitudinal direction by the respective opening zones 12, so the ribbon-like strips 26 do not cover the opening zones 12. The ribbon-like strips 26 do not cover the opening zones 12. The ribbon-like strips 26 bonded to the nonwoven fabric, particularly to the fibers 6 forming the peripheral walls 27 of the opening zones 12 and the protuberance 14 serve to protect these opening zones 12 and protuberance 14 serve to protect these opening zones 12 and protuberance 14 from getting out of shape during use of the napkin 1. Each pair of the adjacent ribbon-like strips 26 are preferably connected to each other by bridges 32 extending in the transverse direction x so that a relative movement of these ribbon-like strips 26 can be restrained and a distance between them can be reliably maintained. The translucent or opaque ribbon-like strips 26 may be used to conceal the core 4 which was sailed with menstrual discharge absorbed therein.

Figure 7:
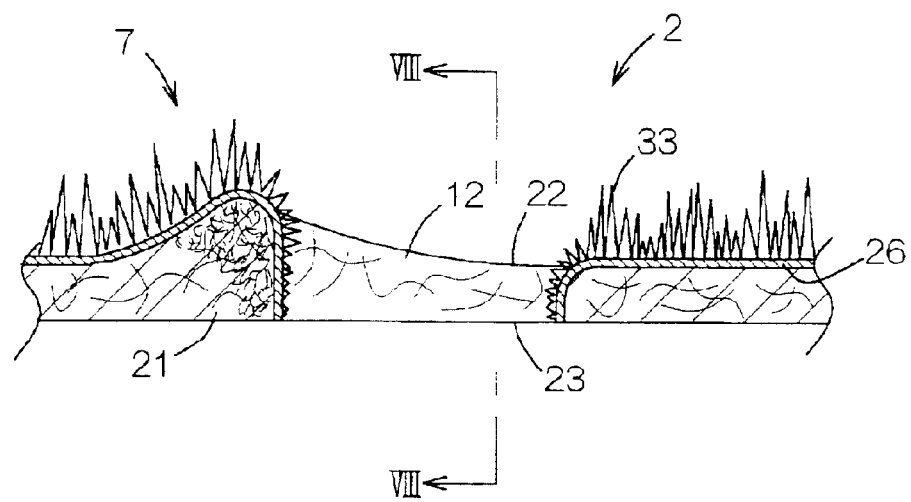
FIG. 7 is a view similar to that in FIG. 5, showing still another embodiment of the invention.
Figure 8:
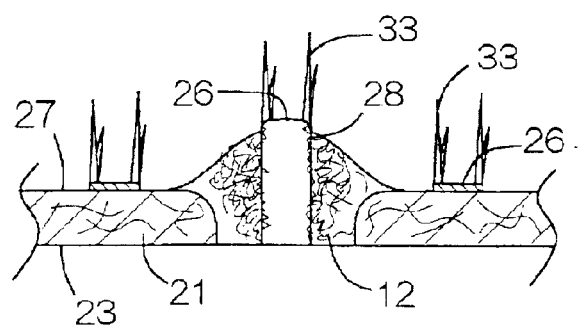
FIG. 8 is a sectional view taken along a line VIII—VIII in FIG. 7.

FIG. 7 is a view similar to FIG. 5 but showing still another embodiment of the invention and FIG. 8 is a sectional view taken along a line VIII—VIII in FIG. 7. In the topsheet 2 according to this embodiment, the film forming the ribbon-like strips 26 is fibrillated along the side edges 28 of the respective ribbon-like strips 26 to form a plurality of fine naps 33 rising toward the direction above the upper surface 22 of the nonwoven fabric layer 21. Such ribbon-like strips 26 offer velvet-like touch. The ribbon-like strips 26 having the naps 33 on the side edges thereof are similar to those described in Japanese Patent Application Publication No. 2000-225144A and preferably have a thickness of about 0.001–0.05 mm, a width of about 0.03–3 mm and spaced about 0.1–5 mm apart each other. The naps 33 have a height of with 0.02–5 mm and are formed in the longitudinal direction y with a density of about 10–100 naps/cm.

While this invention has been described above with respect to the sanitary napkin 1, the topsheet 2 according to this invention is suitable also as the topsheet for other articles such as a disposable diaper, disposable training pants, disposable incontinent pants and a disposable gown used in medical facilities which particularly require breathable topsheets or breathable liquid-pervious topsheets. The nonwoven fabric forming such topsheet 2 may be formed by bonding or mechanically entangling the fibers 6 together. In the napkin 1 illustrated as the one embodiment of this invention, the backsheet 3 comprises the thermoplastic synthetic resin film and the core 4 comprises fluff pulp or a mixture of fluff pulp and high water absorption polymer grains covered with tissue paper 5 (See FIG. 1). For implementation of this invention, a thickness of the nonwoven fabric was measured under a load of 3 g.

The topsheet according to this invention has a plurality of the protuberances each formed on a part of the opening zone's peripheral edge, so it is not apprehended that the opening zones might be closed by the wearer's skin even when these opening zones come in contact with the wearer's skin. In this way, the liquid-permeability of the opening zones as well as the breathability in the vicinity of these opening zones are reliably ensured.

What is claimed is:

1. A topsheet for disposable wearing articles which comprises:
   a nonwoven fabric having an upper surface and a lower surface; and
   a plurality of openings formed in said nonwoven fabric, said plurality of openings extending through both said upper and lower surfaces,
   each of said plurality of openings having an area of about 0.16–5 mm$^2$ and a periphery portion adjacent said upper surface in which only a part of the periphery portion has an increased thickness as compared to an adjacent thickness of said nonwoven fabric so as to form protuberances that extend upward from said upper surface, said protuberances having a density which is higher than a density of surrounding portions of said nonwoven fabric extending around said protuberances.

2. The topsheet according to claim 1, wherein said nonwoven fabric has a longitudinal direction and a transverse direction both orthogonal to a thickness direction of said nonwoven fabric and said protuberances are formed aside of said plurality of openings in one of said longitudinal and transverse directions.

3. The topsheet according to claim 1, wherein said protuberances have a thickness which is about 0.1–2 mm greater than a thickness of the adjacent thickness of said nonwoven fabric.

4. The topsheet according to claim 1, wherein a total area of said plurality of openings occupies 2–60% of a surface area of said nonwoven fabric.

5. The topsheet according to claim 1, wherein said nonwoven fabric is made of thermoplastic synthetic fiber.

6. The topsheet according to claim 1, wherein said upper surface of said nonwoven fabric is covered with a plurality of ribbon-like thermoplastic synthetic resin film strips spaced in parallel to one another and extending in one of said longitudinal direction and a transverse direction.

7. A topsheet for disposable wearing articles which comprises:
   a nonwoven fabric having an upper surface and a lower surface; and
   a plurality of openings formed in said nonwoven fabric, said plurality of openings extending through both said upper and lower surfaces,
   each of said plurality of openings having an area of about 0.16–5 mm$^2$ and a periphery portion adjacent said upper surface in which only a part of the periphery portion has an increased thickness as compared to an adjacent thickness of said nonwoven fabric so as to form protuberances that extend upward from said upper surface, each of said plurality of openings further having opposed first and second sides and opposed first and second ends and said plurality of protuberances being located exclusively along the first ends of each of the plurality of openings.

8. The topsheet according to claim 7, wherein said nonwoven fabric has a longitudinal direction and a transverse direction both orthogonal to a thickness direction of said nonwoven fabric and said protuberances are formed aside of said plurality of openings in one of said longitudinal and transverse directions.

9. The topsheet according to claim 7, wherein said protuberances have a thickness which is about 0.1–2 mm greater than a thickness of the adjacent thickness of said nonwoven fabric.

10. The topsheet according to claim 7, wherein said protuberances have a density which is higher than a density of surrounding portions of said nonwoven fabric extending around said protuberances.

11. The topsheet according to claim 7, wherein a total area of said plurality of openings occupies 2–60% of a surface area of said nonwoven fabric.

12. The topsheet according to claim 7, wherein said nonwoven fabric is made of thermoplastic synthetic fibers.

13. The topsheet according to claim 7, wherein said upper surface of said nonwoven fabric is covered with a plurality of ribbon-like thermoplastic synthetic resin film strips spaced in parallel to one another and extending in one of a longitudinal direction and a transverse direction.

* * * * *